United States Patent [19]

Hatano et al.

[11] 4,316,026

[45] Feb. 16, 1982

[54] PROCESS FOR THE PREPARATION OF COPPER QUINOLINATE

[75] Inventors: Yoshihiro Hatano, Osaka; Seishi Ikegami; Kenji Itoh, both of Yao; Mansuke Matsumoto, Amagasaki, all of Japan

[73] Assignee: Yamamoto Kagaku Gosei Co., Ltd., Yao, Japan

[21] Appl. No.: 177,694

[22] Filed: Aug. 12, 1980

[30] Foreign Application Priority Data

Aug. 14, 1979 [JP] Japan .................. 54-102756

[51] Int. Cl.³ ........................................ C07D 213/807
[52] U.S. Cl. ........................................ 546/5; 546/321
[58] Field of Search .............................. 546/5, 321

[56] References Cited

U.S. PATENT DOCUMENTS

2,371,691  3/1945  Hawkinson ...................... 546/5
2,487,874  11/1949  Huber et al. ..................... 546/5
2,586,555  2/1952  Mueller ............................ 546/5
3,829,432  8/1974  Hanotier et al. ................. 546/5

FOREIGN PATENT DOCUMENTS

945147  7/1956  Fed. Rep. of Germany.
1010524  6/1957  Fed. Rep. of Germany.

OTHER PUBLICATIONS

Stix et al., Chem Ber. 65, 11–13 (1932).
Schwarz, Chem Abs. 53, 18970h (1957).
Van de Kamp, Chem Abs. 42, 3783b (1947).
Chemical Abstracts, vol. 88, 22560b (1978).

Primary Examiner—Mark L. Berch
Attorney, Agent, or Firm—E. Frank McKinney; Paul S. Phillips, Jr.

[57] ABSTRACT

A process for the preparation of copper quinolinate in which quinoline is oxidized by hydrogen peroxide in 10 to 30% sulfuric acid in the presence of copper sulfate at a temperature of 55° to 75° C., the molar ratio of sulfuric acid to quinoline being greater than 1:1. The concentration and amount of sulfuric acid enable greater control of the reaction temperature and result in copper quinolate in improved yield and purity.

Copper quinolinate is used to prepare quinolinic acid which is the starting material for some chromogenic materials used in the pressure-sensitive record material field.

7 Claims, No Drawings

PROCESS FOR THE PREPARATION OF COPPER QUINOLINATE

This invention relates to a process for the preparation of copper quinolinate.

Quinolinic acid is assuming increasing importance in the pressure-sensitive record material art where it is needed as a starting material for the synthesis of some chromogenic materials, such as the pyridinone materials disclosed in U.S. Pat. No. 3,775,424 which is hereby incorporated by reference. In such a process, quinolinic acid is converted to the anhydride such as by reaction with acetic anhydride at 130° C. for 10 minutes. The resulting 2,3-pyridine dicarboxylic anhydride can then be reacted with an indole such as disclosed in Example VI of U.S. Pat. No. 3,775,424.

Quinolinic acid is readily prepared from copper quinolinate by reaction with hydrogen sulfide or sodium hydroxide but the preparation of copper quinolinate itself leaves considerable scope for improvement.

Copper quinolinate has hitherto been obtained by the process described by Stix and Bulgatsch in Chem. Ber., 1932, 65, 11, hereinafter referred to as the Stix process, and comprises the oxidation of quinoline with hydrogen peroxide in sulfuric acid in the presence of copper sulfate. However, the temperature at which the oxidation is carried out is very difficult to control, resulting in a violent exothermic reaction which tends to runaway. It also results in copper quinolinate of low purity and yield; indeed on repetition of the Stix process, a yield of only 44.7% was obtained. Further, the resulting reaction media left after isolation of copper quinolinate is not suitable for re-use in a subsequent run of the process, leading to problems with recovery or waste disposal or the materials present, in particular sulfuric acid and a large amount of copper ions. The Stix process is not therefore suitable for the preparation of copper quinolinate cheaply on an industrial scale.

It has now been found that the use of sulfuric acid in an amount in excess of the amount of quinoline and in a concentration within the range of from 10 to 30% unexpectedly results in a considerable improvement in the Stix process. In particular there is much greater control of the reaction temperature and a much higher yield and purity of the desired copper quinolinate can be obtained.

The present invention therefore provides a process for the preparation of copper quinolinate by oxidizing quinoline with hydrogen peroxide in sulfuric acid in the presence of copper sulfate at a temperature of 55° to 75° C. and isolating copper quinolinate from the reaction media, characterised in that the molar ratio of sulfuric acid to quinoline is greater than 1 to 1 and that the concentration of sulfuric acid is from 10 to 30%.

The temperature of the oxidation reaction is required to be kept within the range of from 55° to 75° C. This is because at temperatures below 55° C. the reaction is very slow requiring a long time to reach completion, whilst at temperatures above 75° C. the reaction proceeds too rapidly becoming uncontrollable and tending to runaway. In the prior art Stix process, it is extremely difficult to control the reaction temperature and keep it within this range. In contrast, the present invention, and in particular the use of a molar ratio greater than 1:1 (sulfuric acid: quinoline), greatly facilitates such control and thus enables the process to be used industrially with much less risk of a runaway reaction occurring.

As mentioned previously, the process of the present invention also enables copper quinolinate to be obtained in increased yield and purity. This is particularly due to the use of sulfuric acid in the process in a concentration within 10 to 30%. At concentrations of less than 10%, the purity of the copper quinolinate is impaired whilst at concentrations of more than 30%, the yield drops.

A further improvement in the yield of copper quinolinate can be achieved if the molar ratio of hydrogen peroxide: quinoline is greater than 10.8:1. There is no upper limit on the relative amount of hydrogen peroxide which can be used but, as no additional improvement in the yield is obtained beyond the use of 13.5 moles of hydrogen peroxide per mole of quinoline, the preferred range is from 10.8:1 to 13.5:1 (hydrogen peroxide:quinoline).

The amount of copper sulfate to be used in the process of the present invention is preferably greater than 0.4 moles per mole of quinoline.

An additional advantage of the present invention when the molar ratio of hydrogen peroxide:quinoline is greater than 10.8:1 is that the resulting reaction media left after isolation of copper quinolinate can be repeatedly used in subsequent process runs. Indeed the same reaction media can be used at least ten times in this way and surprisingly affords a sustained improvement in the yield of copper quinolinate. As a result the process can be carried out even more cheaply as increased yields are obtained on repetition and as any unutilized material present in the media is recycled. In addition, the repeated use of the media considerably minimises the problems normally associated with waste disposal of sulfuric acid and copper ions.

In re-use of the media, the amount of copper sulfate present is supplemented by an amount which is equivalent to the amount of copper quinolinate formed in the previous process run. In this way, copper quinolinate can be obtained in almost quantitative yields based on the supplemented amount of copper sulfate. As sulfuric acid is liberated during the process in an amount which is equivalent to the amount of copper quinolinate formed, it is preferred to supplement the amount of copper sulfate by adding to the media copper oxide or hydroxide so as to produce the copper sulfate in situ. The reason for this is that copper oxide or hydroxide can be recovered as a by-product when copper quinolinate is converted into quinolinic acid with sodium hydroxide. As the copper compounds are the most expensive of the materials used in the present process, the use of the by-product in this way is most economical.

It may be necessary to concentrate the reaction media to be re-used in order to adjust the concentration of the sulfuric acid to within the range of 10-30%. To facilitate this it is preferred that the hydrogen peroxide is used in the preceding process in a concentrated form so as to minimise the volume of the media. However, the concentration of hydrogen peroxide is not critical to the performance of the invention.

After supplementing the amount of copper sulfate and adjusting the concentration of sulfuric acid, the required amounts of quinoline and hydrogen peroxide are added to the media and the process repeated.

Copper quinolinate can exist in two forms—2:1 copper quinolinate (formula (I)) in which two molecules of quinoline are combined with one atom of copper, and 1:1 copper quinolinate (formula (II)) in which one molecule of quinoline is combined with one atom of copper.

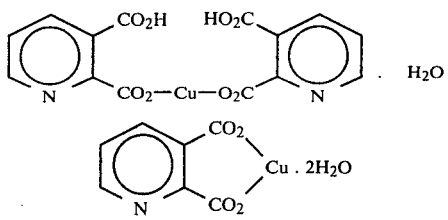

Both of these forms can be prepared by the present process depending on the molar ratio of copper sulfate to sulfuric acid. If the ratio is less than or equal to 0.5, the 2:1 copper quinolinate (I) is formed, whereas, if the ratio is greater than 0.5, then the 1:1 copper quinolinate (II) is formed. However, the 2:1 copper salt (I) is preferred since less copper is employed.

The present invention will now be described in more detail with reference to a number of examples, in which all parts and percentages are by weight.

EXAMPLE 1

Preparation of 2:1 Copper Quinolinate

To 180 parts of water were added 10–120 parts of concentrated sulfuric acid, followed by the successive addition of 25 parts of crystalline copper sulfate, 25.8 parts of quinoline, and 122.4 parts of 60% hydrogen peroxide, and then the resulting mixture was allowed to react at 60°–70° C. for 5 hours with stirring. After cooling, the precipitated 2:1 copper quinolinate (I) was filtered, washed with water, and dried.

The results are shown in Table 1, in which the molar ratio is the number of moles of sulfuric acid per mole of quinoline and in which the concentration of sulfuric acid is that obtained after addition to the water.

TABLE 1

| Sulfuric acid | | | 2:1 Copper quinolinate | | |
|---|---|---|---|---|---|
| Conc. $H_2SO_4$ added (parts) | Molar ratio | Concentration (%) | Yield (parts) | Yield (%) | powder appearance |
| 10 | 0.5 | 5.6 | 18.9 | 45.7 | Greenish brown |
| 20 | 1.0 | 10.0 | 27.3 | 66.0 | Blue |
| 30 | 1.5 | 14.3 | 27.6 | 66.7 | Blue |
| 40 | 2.0 | 18.2 | 26.7 | 64.6 | Blue |
| 50 | 2.5 | 21.7 | 26.1 | 63.1 | Blue |
| 60 | 3.0 | 25.0 | 25.6 | 61.9 | Blue |
| 120 | 6.0 | 40.0 | 21.3 | 51.5 | Blue |

When the molar ratio of sulfuric acid was less than 1.0 and the concentration was less than 10%, the control of the reaction temperature became difficult, and the copper quinolinate was low in yield and purity as evidenced by the greenish brown powder which was obtained. At the other end, when the concentration of sulfuric acid was more than 40%, the yield of copper quinolinate decreased owing to its dissolution in sulfuric acid.

EXAMPLE 2

Preparation of 2:1 Copper Quinolinate

To 180 parts of water and 50 parts of concentrated sulfuric acid were added 20–50 parts of crystalline copper sulfate, followed by the addition of 25.8 parts of quinoline and 122.4 parts of 60% hydrogen peroxide, and then the resulting mixture was allowed to react at 60°–70° C. for 5 hours with stirring. After cooling, the precipitated 2:1 copper quinolinate (I) was filtered, washed with water, and dried.

The results are shown in Table 2, in which the molar ratio is the number of moles of copper sulfate per mole of quinoline.

TABLE 2

| Crystalline copper sulfate | | | 2:1 Copper quinolinate | | |
|---|---|---|---|---|---|
| Amount added (parts) | Molar ratio | $CuSO_4:H_2SO_4$ | Yield (parts) | Yield (%) | powder appearance |
| 20 | 0.4 | 0.16 | 25.2 | 60.9 | Blue |
| 25 | 0.5 | 0.2 | 26.1 | 63.1 | Blue |
| 50 | 1.0 | 0.4 | 25.6 | 61.9 | Blue |

These results confirm that, when the molar ratio of copper sulfate:sulfuric acid is less than or equal to 0.5, 2:1 copper quinolinate is formed.

EXAMPLE 3

Preparation of 2:1 Copper Quinolinate

To 180 parts of water and 50 parts of concentrated sulfuric acid were added 25 parts of crystalline copper sulfate, followed by the addition of 25.8 parts of quinoline, and 102–153 parts of 60% hydrogen peroxide, and then the resulting mixture was allowed to react at 60°–70° C. for 5 hours with stirring. After cooling, the precipitated 2:1 copper quinolinate was filtered, washed with water, and dried.

The results are shown in Table 3, in which the molar ratio is the number of moles of hydrogen peroxide per mole of quinoline.

TABLE 3

| 60% Hydrogen peroxide | | 2:1 Copper quinolinate | | |
|---|---|---|---|---|
| Amount added (parts) | Molar ratio | Yield (parts) | Yield (%) | powder appearance |
| 102.0 | 9.0 | 21.5 | 52.0 | Blue |
| 112.2 | 9.9 | 23.3 | 56.4 | Blue |
| 122.4 | 10.8 | 26.1 | 63.1 | Blue |
| 132.6 | 11.7 | 27.1 | 65.5 | Blue |
| 142.8 | 12.6 | 27.7 | 67.0 | Blue |
| 153.0 | 13.5 | 28.2 | 68.2 | Blue |

When the molar ratio was less than 9.9 the filtrate was colored brown, so that the reaction media was not suitable for re-use. On the other hand, when the molar ratio was more than 10.8, the media was colored green, so that it was possible to re-use it in the process more than ten times.

EXAMPLE 4

Preparation of 2:1 Copper Quinolinate by Repeated use of Reaction Media

First process: To 180 parts of water and 60 parts of concentrated sulfuric acid were added 8 parts of copper oxide, and the resulting mixture was stirred at 80°–90° C. for 30 minutes, whereby the copper oxide was completely converted into copper sulfate. After cooling to 50° C., 25.8 parts of quinoline and 122.4 parts of 60% hydrogen peroxide were added, and then the reaction was carried out at 60°–70° C. for 5 hours with stirring. After cooling, the precipitated 2:1 copper quinolinate was filtered, washed with water, and dried, giving 27 parts of the product in a yield of 65.3%.

Second process: After 5.2 parts of copper oxide had been added to the filtrate and the washings of the first reaction, the resulting mixture was concentrated to about 230 parts, whereby the copper oxide was completely converted into copper sulfate. After cooling to 50° C., 25.8 parts of quinoline and 122.4 parts of 60% hydrogen peroxide were added, and then the reaction was carried out at 60°–70° C. for 5 hours with stirring. After cooling, the precipitated 2:1 copper quinolinate was filtered, washed with water, and dried, giving 30 parts of copper quinolinate in a yield of 72.6%.

The third process et seq. were carried out in essentially the same manner as described for the second process.

The results are shown in Table 4.

TABLE 4

| Process | Reaction Media | Copper oxide (parts) | 2:1 Copper quinolinate Yield (parts) | Yield (%) | Powder appearance |
|---|---|---|---|---|---|
| 1 | Water 180 parts + conc. H$_2$SO$_4$ 60 parts* | 8.0 | 27.0 | 65.3 | Blue |
| 2 | Resulting media + washings of 1st reaction | 5.2 | 30.0 | 72.6 | Blue |
| 3 | "2nd" | 5.8 | 31.0 | 75.0 | Blue |
| 4 | "3rd" | 6.0 | 30.9 | 74.7 | Blue |
| 5 | "4th" | 5.9 | 31.6 | 76.4 | Blue |
| 6 | "5th" | 6.1 | 31.2 | 75.5 | Blue |
| 7 | "6th" | 6.0 | 31.5 | 76.2 | Blue |
| 8 | "7th" | 6.1 | 31.9 | 77.1 | Blue |
| 9 | "8th" | 6.2 | 32.6 | 78.8 | Blue |
| 10 | "9th" | 6.3 | 31.9 | 77.1 | Blue |

(*10 parts of 60 parts of concentrated sulfuric acid are used for conversion of copper oxide into copper sulfate.)

The yield of the first process was less than 70%, but subsequent yields were appreciably higher.

EXAMPLE 5

Preparation of 1:1 Copper Quinolinate (II) by Repeated Use of Reaction Media

First Process: 39.8 parts of copper oxide were added to 350 parts of water and 100 parts of concentrated sulfuric acid, and stirred at 80°–90° C. for 30 minutes, whereby the copper oxide was completely converted into copper sulfate. After cooling to 50° C., 25.8 parts of quinoline and 150 parts of 60% hydrogen peroxide were added, and then the reaction was carried out at 60°–70° C. for 3 hours with stirring. After cooling, the precipitated 1:1 copper quinolinate was filtered, washed with water, and dried, giving 31.2 parts of copper quinolinate in a yield of 59.0%.

Second process: After 9.4 parts of copper oxide had been added to the filtrate and the washings of the first reaction the resulting mixture was concentrated to about 400 parts, whereby the copper oxide was completely converted into copper sulfate. After cooling to 50° C., 25.8 parts of quinoline and 150 parts of 60% hydrogen peroxide were added, and then the reaction was carried out at 60°–70° C. for 3 hours with stirring. After cooling, the precipitated 1:1 copper quinolinate was filtered, washed with water, and dried, giving 37.4 parts of copper quinolinate in a yield of 70.7%.

The third process et seq. were carried out in essentially the same way as described for the second process. The results are shown in Table 5.

TABLE 5

| Process | Reaction Media | Copper oxide (parts) | 1:1 Copper quinolinate Yield (parts) | Yield (%) | Powder appearance |
|---|---|---|---|---|---|
| 1 | Water 150 parts + conc. H$_2$SO$_4$ 100 parts* | 39.8 | 31.2 | 59.0 | Blue |
| 2 | Resulting media + washings of 1st reaction | 9.4 | 37.4 | 70.7 | Blue |
| 3 | "2nd" | 11.3 | 37.7 | 71.3 | Blue |
| 4 | "3rd" | 11.4 | 38.5 | 72.8 | Blue |
| 5 | "4th" | 11.6 | 37.6 | 71.1 | Blue |
| 6 | "5th" | 11.3 | 39.7 | 75.0 | Blue |
| 7 | "6th" | 12.0 | 39.2 | 74.1 | Blue |
| 8 | "7th" | 11.9 | 39.3 | 74.3 | Blue |
| 9 | "8th" | 11.9 | 39.6 | 74.9 | Blue |
| 10 | "9th" | 12.0 | 39.8 | 75.2 | Blue |

(*50 parts of 100 parts of concentrated sulfuric acid are used for conversation of copper oxide into copper sulfate).

The yield of the first process was less than 70%, but subsequent yields were appreciably higher.

COMPARATIVE EXAMPLE

Preparation of 1:1 copper quinolinate (II) by the Stix process 24 g of quinoline, 2100 ml of 3% hydrogen peroxide, and 46 g of 25% sulfuric acid were heated to 60° C. and 64 g of crystalline copper sulfate dissolved in 160 ml of water were added thereto. As the temperature began to rise after a few minutes, the system was strongly cooled with ice water so as to maintain the temperature below 70° C. However the control of the temperature was extremely difficult, and after the violent exothermic reaction subsided, the reaction was continued for 8 hours at 65°–70° C. Then 200 ml of 3% hydrogen peroxide was added and the reaction was continued for a further 3 hours at 65°–70° C. After cooling, the precipitated 1:1 copper quinolinate was filtered, washed with water, and dried, giving 22 g of product in a yield of 44.7%. The 1:1 copper quinolinate obtained was greenish black and low in purity.

Also, the resulting reaction media left after filtration of the copper quinolinate was dark brown, and its re-use as the reaction media was most undesirable as the purity and the yield of the resulting product would seriously suffer and a runaway reaction would tend to occur.

REFERENCE EXAMPLE

Preparation of quinolinic acid from copper quinolinate 1. 20.7 parts of 2:1 copper quinolinate obtained in accordance with the procedure of Example 1 were dispersed in 500 parts of water with stirring, and hydrogen sulfide was passed through at 60° C. until the blue colour of the copper quinolinate had been fully replaced by the black colour of the liberated copper sulfide. After the copper sulfide had been filtered off, the filtrate was concentrated, and 15.2 parts (91%) of yellow quinolinic acid was obtained.

2. 26.5 g of 1:1 copper quinolinate obtained in accordance with the procedure of Example 5, 9.6 parts of sodium hydroxide, and 190 parts of water were allowed to react at 80° C. for 1 hour with stirring. After cooling, the copper oxide formed was filtered off, and the filtrate was acidified with dilute sulfuric acid and then concentrated, giving 15.7 parts (94%) of yellow quinolinic acid.

What is claimed is:

1. A process for the preparation of copper quinolinate by oxidizing quinoline with hydrogen peroxide in a mixture of water and sulfuric acid in the presence of copper sulfate at a temperature of 55° to 75° C. and isolating copper quinolinate from the reaction media, wherein the molar ratio of sulfuric acid to quinoline is greater than 1 to 1, the molar ratio of hydrogen peroxide to quinoline is 10.8 to 1 or greater and the concentration of sulfuric acid is from about 10 to about 30% in said mixture.

2. A process according to claim 1, wherein the molar ratio of hydrogen peroxide to quinoline is greater than 10.8 to 1.

3. A process according to claim 2, wherein the molar ratio of copper sulfate to quinoline is greater than 0.4 to 1.

4. A process according to claim 2, wherein quinoline and hydrogen peroxide are added to the reaction media left after isolation of copper quinolinate prepared according to a previous run of the process according to claim 3, the amount of copper sulfate present in the media having been supplemented by an amount equivalent to the amount of copper quinolinate prepared in the previous run and the concentration of sulfuric acid present in the media having been adjusted to within the range of 10 to 30%.

5. A process according to claim 4, wherein copper oxide or hydroxide is added to the media so as to produce, by reaction with the sulfuric acid, the copper sulfate in situ.

6. A process according to claim 1, 2, 3, 4 or 5 wherein 2:1 copper quinolinate or 1:1 copper quinolinate is selectively prepared by adjusting the molar ratio of copper sulfate to sulfuric acid.

7. A process according to claim 6, wherein 2:1 copper quinolinate is prepared by using a molar ratio of copper sulfate to sulfuric acid which is less than or equal to 0.5.

* * * * *

UNITED STATES PATENT AND TRADEMARK OFFICE
CERTIFICATE OF CORRECTION

PATENT NO. : 4,316,026
DATED : February 16, 1982
INVENTOR(S) : Yoshihiro Hatano et al.

It is certified that error appears in the above-identified patent and that said Letters Patent are hereby corrected as shown below:

Abstract, line 8 change "late" to --linate--.

Signed and Sealed this

Fourth Day of May 1982

[SEAL]

Attest:

Attesting Officer

GERALD J. MOSSINGHOFF

Commissioner of Patents and Trademarks